United States Patent [19]

Katz

[11] 4,087,364

[45] May 2, 1978

[54] LIQUID SLURRY OF SUBMICRON PARTICLES OF HEXABROMOBENZENE, AND PROCESS OF MANUFACTURE

[75] Inventor: Daniel Stanley Katz, Norwalk, Conn.

[73] Assignee: American Cyanamid Company, Stamford, Conn.

[21] Appl. No.: 732,619

[22] Filed: Oct. 15, 1976

Related U.S. Application Data

[63] Continuation of Ser. No. 327,058, Jan. 26, 1973, abandoned, which is a continuation-in-part of Ser. No. 265,120, Jun. 22, 1972, abandoned.

[51] Int. Cl.$^2$ ............................................. C07C 25/00
[52] U.S. Cl. ................. 252/8.1; 260/650 R; 260/706; 427/170; 428/921
[58] Field of Search ............... 260/650 R, 706, 898; 23/294, 300; 427/170; 428/921; 252/8.1

[56] References Cited

U.S. PATENT DOCUMENTS

| 1,631,589 | 6/1927 | Grosvenor | 260/706 X |
| 3,480,582 | 11/1969 | Brooks | 260/898 |
| 3,875,108 | 4/1975 | Koch et al. | 428/921 |
| 3,877,974 | 4/1975 | Mischutin | 428/921 |

FOREIGN PATENT DOCUMENTS

| 1,934,155 | 1/1971 | Germany | 260/650 |

*Primary Examiner*—O. R. Vertiz
*Assistant Examiner*—Brian E. Hearn
*Attorney, Agent, or Firm*—Philip Mintz

[57] ABSTRACT

A liquid slurry of submicron particles of hexabromobenzene is prepared by vaporizing hexabromobenzene in a first zone, transporting the vapors to a second zone by use of an inert carrier gas, condensing the vapors in a second zone so as to form a liquid slurry, and thereafter recovering the slurry formed. The product particles are particularly effective when used as a fire retardant in an acrylic fiber having high luster requirements.

8 Claims, No Drawings

LIQUID SLURRY OF SUBMICRON PARTICLES OF HEXABROMOBENZENE, AND PROCESS OF MANUFACTURE

This is a continuation, of application Ser. No. 327,058 filed Jan. 26, 1973, which application was a continuation-in-part of application Ser. No. 265,120, filed June 22, 1972, both now abandoned.

This invention relates to submicron hexabromobenzene particles and to fire-retardant acrylic fibers containing same. More particularly, this invention relates to a liquid slurry of submicron hexabromobenzene particles, to the process therefore which comprises vaporizing, transporting, condensing, and stabilizing said particles, and to acrylic fibers containing fire retardant amounts thereof.

Prior to the present invention, it has been contemplated to form submicron particles by cooling a hot fluid or gas to precipitate the desired particles. For instance, U.S. Pat. No. 3,516,879 issued June 23, 1970 to Robert H. Globus, discloses a method for producing fine particles of less than one micron diameter wherein a gaseous stream containing $ClF_3$ is injected through a small orifice below the surface of a cold, preferably cryogenic, bath, whereby fine particles of $ClF_3$ are produced. This technique, however, has not controllably produced submicron particles of hexabromobenzene, which is used effectively as a fire retardant additive in acrylic fibers. The reason for this is attributable to the use of a non-condensable diluent gas and also to the retention of formed particles in the quench zone. The use of a non-condensable diluent offers no protection against growth of nucleated particles. The retention of formed particles in the quench zone causes growth thereof to relatively large particles by subsequently condensed hexabromobenzene which deposits on these nucleated particles.

Additionally, it is known that certain halogenated organic compounds are useful as fire-retardant additives in acrylic fibers and in other applications. Hexabromobenzene in particulate form is known to be an effective fire-retardant additive, especially when used in conjunction with acrylic fiber. The hexabromobenzene conventionally employed in fiber use is reduced in particle size, generally by mechanical grinding or fluid energy milling. However, the particles of hexabromobenzene thus obtained when used in fiber as fire-retardant additives cause severe delustering of the fiber. This delustering has rendered hexabromobenzene in such forms commercially unattractive as a fire-retardant additive in applications involving carpet and apparel fibers.

In accordance with the present invention, there is provided a liquid slurry of particulate hexabromobenzene, the particles of which have an average diameter of about 100A to about 3000A and are present in the range of about 0.1% to 40%, by weight, based on the total weight of said slurry.

There is also provided a process for preparing particulate hexabromobenzene of an average particle size of about 100A to 3000A, which process comprises: vaporizing hexabromobenzene in a first zone; transporting the vaporized hexabromobenzene to a second zone by means of a carrier gas inert to said hexabromobenzene; condensing the vaporized hexabromobenzene in said second zone to form stabilized particles of a diameter in the range of about 100A to 3000A; and thereafter recovering the stabilized hexabromobenzene particles.

Further, there is also provided an improvement in a fire-retardant acrylic fiber containing from about 1% to 40%, by weight, based on the weight of said fiber, of particulate hexabromobenzene uniformly dispersed therein, the improvement wherein said particles have an average diameter of about 100A to about 3000A whereby the luster of said fiber is enhanced.

In accordance with the present invention, the submicron particles of hexabromobenzene initially formed by vaporization and condensation of hexabromobenzene are stabilized by use of a liquid quench in conjunction with condensation. This liquid quench may arise from use of superheated steam as the carrier gas or from added liquid medium as a quench in the condensation zone or both. The slurry resulting from use of the liquid medium contains particles of hexabromobenzene in the range of about 100A and about 3000A, which particles are stablized against growth by the presence of the liquid medium. The use of the slurried particles in preparation of fire-retardant acrylic fiber by conventional wet-spinning techniques results in enhanced fiber luster compared with that of the same fiber containing other forms of particulate hexabromobenzene.

In carrying out the process of the present invention, a convenient form of hexabromobenzene is employed. This material is available in solid form as crystals or pellets, and may be used as supplied or after grinding to reduce particle size. Hexabromobenzene has the ability to sublime, thus converting from solid to gaseous forms and reverse without the need for going through the liquid state.

In vaporizing hexabromobenzene, the solid is heated sufficiently so as to effect vaporization thereof. The compound undergoes decomposition when heated above about 350° C. and, accordingly, temperatures in excess thereof are to be avoided. At about 180° C. and higher, a desirable degree of vaporization occurs and, accordingly, temperatures in the range of about 180° C. to 350° C. are admirably suitable for vaporization. Although melting of hexabromobenzene occurs at about 316° C., vaporization of the molten compound also occurs so that such condition, although precluding sublimation in the strict sense, does not interfere with processing. The vaporization of hexabromobenzene is carried out in a first processing zone.

As the hexabromobenzene is vaporized in the first reaction zone, a carrier gas is introduced thereto to transport the vaporized hexabromobenzene to a second processing zone. The carrier gas employed must be inert to the hexabromobenzene. Suitable carriers include the so-called "inert" gases as well as air and water vapor. The carrier gas should be at a temperature sufficient to maintain the hexabromobenzene in vaporized form. Accordingly, it is necessary to employ the carrier gas at a temperature in the range of about 180° C. to about 350° C. Water vapor for such use will be in the form of steam. The pressure of the carrier gas stream is not critical, and can be regulated so as to provide the proper gas temperature and adequate transfer of vaporized hexabromobenzene.

In transporting the vaporized hexabromobenzene from the first zone to the second zone, care should be taken to ensure that premature condensation does not occur. Such occurrence not only interfers with process continuity, but causes an increase in particle size of the hexabromobenzene obtained. Accordingly, suitable means to prevent temperature losses due to heat transfer should be employed in the transport area.

After the vaporized hexabromobenzene is transported to the second zone, it is condensed into particulate form. This is accomplished by rapidly cooling the vaporized hexabromobenzene. However, to obtain the desired submicron particles, it is necessary to carry out condensation in conjunction with a non-solvent liquid so as to stabilize the particles formed against extensive growth. The non-solvent liquid may arise as a result of a condensable carrier gas, such as superheated steam. A preferred procedure is to use a cold non-solvent liquid as a quench in the condensation zone. Hexabromobenzene should be substantially insoluble in the non-solvent liquid so as to minimize particle growth. Suitable non-solvent liquids include water, aqueous salt solutions, alcohol, ether, and the like, provided the solubility of hexabromobenzene therein at the temperature of use is less than about 0.01 part per 100 parts of liquid. The liquid quench is run through the condensation zone at a rate adequate to remove submicron particles of hexabromobenzene therefrom. The quench liquid may be used to remove varying contents of submicron particles from the quench zone. It is generally preferable, however, to remove the particles at a rapid rate so as to prevent growth thereof in the condensation zone. Generally, the quench liquid will contain about 0.01% or more by weight thereof of submicron as it leaves the condensation zone. Since residence time in the condensation zone can have an influence on particle size, however, the rate of flow of quench liquor out of the condensation zone should be regulated to provide the particle size desired.

In order to maximize condensation and recovery of vaporized hexambromobenzene in particulate form, it is desirable to cause the quench liquid to flow through a constricted area on its exit from the condensation zone. This modification is designed to prevent sudden expansion of gas and growth of condensed particles.

The quench liquor with its content of submicron particles of hexabromobenzene is recovered after it leaves the condensation zone. It may be used directly as the slurry of submicron particles. It is generally preferable to subject the initial slurry to separation, such as by centrifugation or other methods of separation, so as to concentrate the content of submicron particles. The purified non-solvent liquid can be recycled as quench liquid in the condensation zone. The separated submicron particles of hexabromobenzene are then recovered and adjusted to a desired concentration in slurry form with non-solvent liquid. The broad range of slurry concentration is from about 0.1% to 50%, by weight, of submicron particles of hexabromobenzene based on the total slurry weight. A preferred range is about 10% to 40%, by weight, based on the total slurry weight, since it represents a useful range for providing fire-retardant acrylic fibers.

The process of the present invention is the only method known whereby submicron particles of hexabromobenzene can be obtained in useful form.

The slurry of submicron particles of hexabromobenzene is stable against particle growth over reasonable time periods so that subsequent use thereof in fiber preparation can be accomplished. It is generally preferred to store the slurry at low temperatures to minimize particle growth.

Once the submicron particles are incorporated into acrylic fiber by use of the slurry thereof, the final fiber in its dry form retains the submicron particles at their incorporated size. Thus, the fiber retains its fire retardant in submicron size and its enhanced luster associated therewith indefinitely. In addition to the enhanced luster associated with the submicron particles of fire retardant, the fiber also possesses a favorable balance of other textile properties.

The invention is more fully illustrated by the examples which follow, wherein all parts and percentages are by weight unless otherwise specifically designated.

EXAMPLE 1

Cylindrical pellets of hexabromobenzene, 1 inch long by ¾ inch in diameter were charged into a vaporizer consisting of an electrically heated pipe 12 inches long and 2 inches in diameter. A stream of air at a flow rate of six pounds per hour was passed through the vaporizer as a carrier gas. The air temperature was 220° C. and carried off hexabromobenzene vapor at 265° C. at the rate of 4.6 grams per hour. The carrier gas stream with its content of hexabromobenzene vapor entered a condensation zone through a ceramic tube of 3/16 inch diameter. The condensation zone consisted of a stainless steel cross of ⅜ inch diameter. The carrier gas with its hexabromobenzene vapor content entered the top member of the cross. Through the two side members of the cross were injected twin streams of 12% aqueous sodium thiocyanate at the total rate of 16.6 gallons per hour, both streams flowing into the cross. The streams quenched the hexabromobenzene vapors and formed a slurry therewith which flowed out the bottom member of the cross. On exiting from the bottom of the cross the slurry was constricted by passing through a tube 9 inches long and ¼ inch in diameter. The slurry then flowed into a deaeration tank of ½ liter capacity. The slurry was subsequently centrifuged, yielding a slurry of 20% hexabromobenzene in sodium thiocyanate. The clear sodium thiocyanate solution removed by centrifugation was cooled and recycled to the condensation zone as quench replenishment. The resulting slurry recovered contained hexabromobenzene particles, 90% of which were in the range of 100A to 300A as determined by electron microscopy. This slurry was eminently suitable for use in preparing fire-retardant acrylic fibers.

EXAMPLES 2-3

The procedure of Example 1 was repeated in every material detail except that the quench liquid employed was an 11.7% aqueous solution of sodium thiocyanate. Duplicate runs were made to determine reproducibility of the process. Particle size measurements of the two runs, designated by example numbers, were as follows:

| Run | Peak Particle Size Distribution A |
| --- | --- |
| Example 2 | 150–300 |
| Example 3 | 150–300 |

EXAMPLES 4-5

The procedure of Example 1 was again repeated in every material detail except that the quench liquor was water. Duplicate runs were again made to determine reproducibility of the process. Particle size measurements of the two runs, designated by example numbers, were as follows:

| Run | Peak Particle Size Distribution A |
|---|---|
| Example 4 | 200–500 |
| Example 5 | 250–800 |

These results, coupled with those of Examples 2 and 3, indicate the preference for aqueous salt solutions over water as quench liquors, both from the viewpoints of reproducibility and reduced particle size.

EXAMPLE 6

The procedure of Example 1 was again repeated in every material detail except that steam was used in place of air as the carrier gas. In this example also the quench liquor was water rather than sodium thiocyanate solution. The slurry obtained contained hexabromobenzene of peak particle size in the range of 150–500.

EXAMPLE 7

The slurry of Example 2 was stored for 3 days at 5° C. to determine stability of the particle size of hexabromobenzene therein. The results are summarized as follows:

| Peak Particle Size Distribution A | |
|---|---|
| As Prepared | 3 Days at 5° C. |
| 150–300 | 150–350 |

EXAMPLE 8

In order to evaluate the effects of submicron particles of hexabromobenzene as a fire-retardant additive in acrylic fibers, the particles were incorporated in a typical fiber and compared in performance to a similar fiber prepared with an identical amount of conventional hexabromobenzene particles.

To prepare the fibers, an acrylic copolymer consisting of 89.6% acrylonitrile and 10.4% methyl methacrylate was employed. A spinning dope was prepared so as to contain 12.6% polymer solids, 4% of hexabromobenzene based on the weight of polymer in an aqueous solution of 46% sodium thiocyanate. The hexabromobenzene was uniformly distributed throughout the spinning solution and the polymer solution was then immediately spun into an aqueous solution of 12% sodium thiocyanate maintained at −3° C. to coagulate the fiber. The fiber was water-washed, stretched in hot water, collapsed, heat-relaxed, and subsequently dried in accordance with conventional wet-spinning procedures to provide fiber of 16 deniers. The fiber was then processed into yarn and knitted fabric was prepared therefrom for testing.

Using the above procedure, three knitted fabrics were prepared, one employing the slurry of hexabromobenzene particles prepared in Example 1 (Example 9), a second containing hexabromobenzene of peak particle size distribution of 2 microns (comparative) and a third containing no hexabromobenzene additive.

The test performed on the samples were as follows:

Limiting Oxygen Index

The minimum oxygen percent in a non-combustible gas required to support combustion of a plain jersey knit having a density of 4.5 ounces per square yard prepared from an 18 singles yarn of the fiber under test.

Fiber luster

A sample of fiber is wound tightly around a flat plate with winds parallel to one another. The plate is placed on an abridged spectrophotometer. The plate is then rotated in its own plane through 360°. The difference between the highest and lowest measurements of reflectance in percent measured during sample rotation is then determined. The difference calculated for the blank sample is arbitrarily assigned a luster value of 100. The differences calculated for the samples containing hexabromobenzene are then assigned luster values in percent based on their relation to the difference calculated for the blank.

Light Transmission

The light transmitted through a 2.5% suspension of test fibers ⅜ inch in length and containing hexabromobenzene therein in a liquid whose refractive index matches that of the fiber without additive expressed as a percentage of the light transmitted through a similar suspension of fibers without additive.

The results of these determinations are given in the table which follows:

| Fiber Sample | Limiting Oxygen Index | Relative Fiber Luster | Relative Light Transmission |
|---|---|---|---|
| Example 9 | 21.2 | 50% | 55% |
| Comparative | 20.8 | 23% | 25% |
| Blank | 19.6 | 100% | 100% |

These results show that the fire-retardant fibers of the present invention are not only improved in light transmission and limiting oxygen index over comparative fibers, but also possess greatly enhanced fiber luster.

I claim:

1. An aqueous slurry of particulate hexabromobenzene, the particles of which have an average diameter between about 100A and 3000A and are present in an amount from about 0.1 to 40%, by weight, based on the total weight of said slurry.

2. The slurry of claim 1 wherein the liquid thereof is an aqueous solution of sodium thiocyanate and said particles have a peak particle size distribution between 150A and 300A.

3. The slurry of claim 1 wherein said hexabromobenzene particles have a peak particle size distribution between 150A and 800A.

4. The slurry of claim 3 wherein said hexabromobenzene particles have a peak particle size distribution between 200A and 500A.

5. The slurry of claim 3 wherein said hexabromobenzene particles have a peak particle size distribution between 250A and 800A.

6. The slurry of claim 3 wherein said hexabromobenzene particles have a peak particle size distribution between 150A and 500A.

7. A process for preparing particulate hexabromobenzene of an average particle diameter of about 100A to 3000A, which process comprises: vaporizing hexabromobenzene in a first zone at a temperature of from about 180° C.–350° C.; transporting the vaporized hexabromobenzene to a second zone by means of a carrier gas consisting of air or steam at a temperature of from about 180° C.–350° C.; condensing the vaporized hexabromobenzene in said second zone by an aqueous sodium thiocyanate solution quench medium to form stabilized particles of a diameter in the range of about 100A to 3000A; and thereafter recovering the stabilized hexabromobenzene particles.

8. The process of claim 7 wherein said carrier gas is steam.

* * * * *